US00PP34744P2

(12) United States Plant Patent
Hartman

(10) Patent No.: US PP34,744 P2
(45) Date of Patent: Nov. 15, 2022

(54) ***CALADIUM* PLANT NAMED 'CRM FCY OF15-76'**

(50) Latin Name: ***Caladium* X *hortulanum***
Varietal Denomination: CRM FCY OF15-76

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 17/741,052

(22) Filed: May 10, 2022

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 6/10; A01H 5/12
See application file for complete search history.

*Primary Examiner* — Keith O. Robinson
(74) *Attorney, Agent, or Firm* — C. Anne Whealy

(57) ABSTRACT

A new and distinct cultivar of *Caladium* plant named 'CRM FCY OF15-76', characterized by its intermediate and upright to mounding plant habit; dense, leafy and bushy appearance; vigorous growth habit and rapid growth rate; fancy-type leaves that are creamy to greenish white in color variably flushed with pink, variably covered with random pink and/or white-colored spots and proximally, variably mottled with dark green-colored markings; and petioles that are almost black in color with green or tannish brown-colored stripes and/or greenish brown-colored stippling, streaks and stripes.

5 Drawing Sheets

Figure 1:
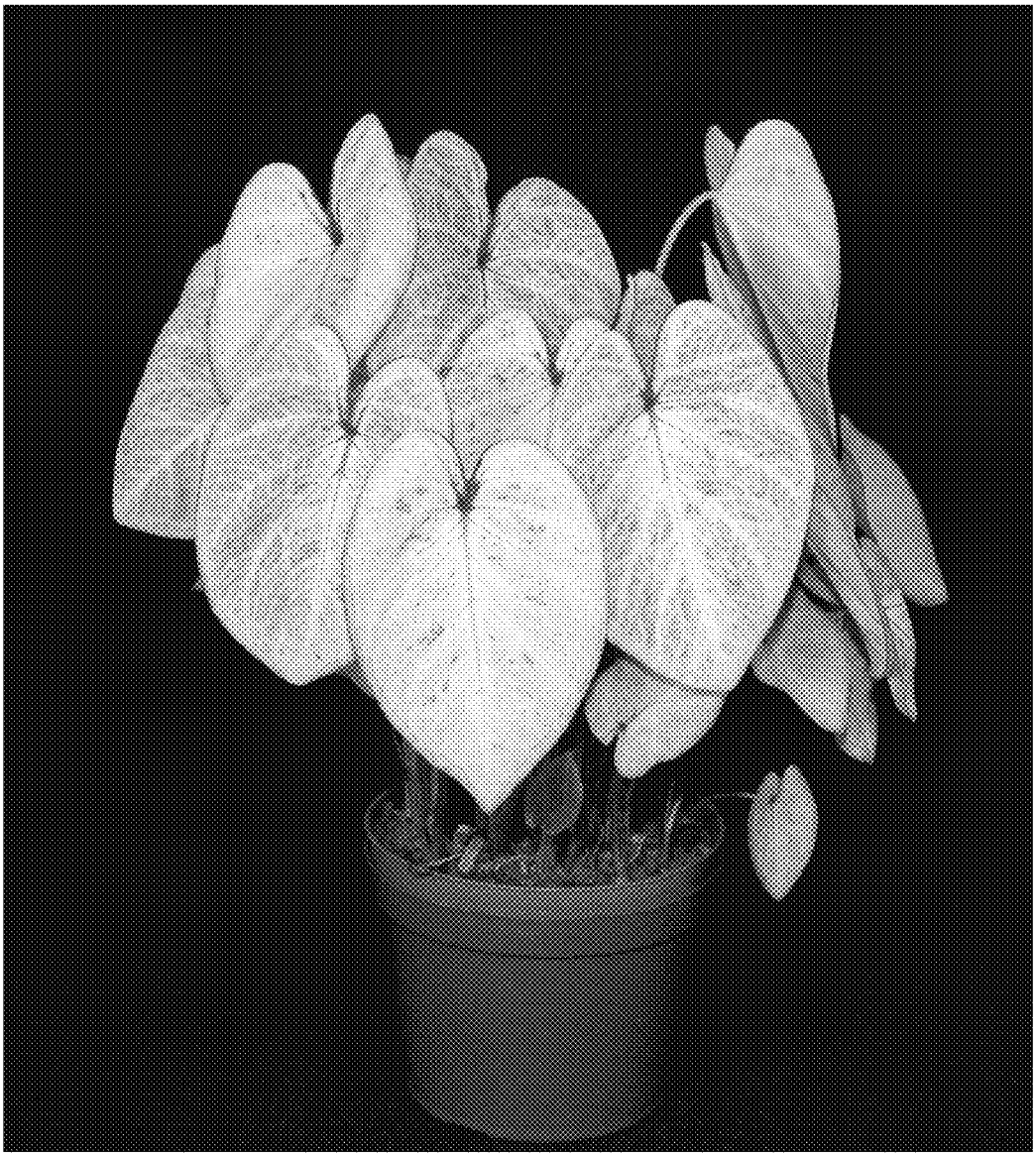

Botanical designation: *Caladium* X *hortulanum*.
Cultivar denomination: 'CRM FCY OF15-76'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'CRM FCY OF15-76'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2014 in Avon Park, Fla. of *Caladium* X *hortulanum* 'Florida Moonlight', disclosed in U.S. Plant Pat. No. 14,565, as the female, or seed, parent with *Caladium* X *hortulanum* 'Splash of Wine', disclosed in U.S. Plant Pat. No. 31,599, as the male, or pollen, parent. The new *Caladium* plant was discovered and selected by the Inventor as a single plant within the progeny of the stated cross-pollination in a controlled outdoor nursery environment in Avon Park, Fla. in September, 2015.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2016 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'CRM FCY OF15-76'. These characteristics in combination distinguish 'CRM FCY OF15-76' as a new and distinct *Caladium* plant:

1. Intermediate and upright to mounding plant habit; dense, leafy and bushy appearance.
2. Vigorous growth habit and rapid growth rate.
3. Fancy-type leaves that are creamy to greenish white in color variably flushed with pink, variably covered with random pink and/or white-colored spots and proximally, variably mottled with dark green-colored markings.
4. Petioles that are almost black in color with green or tannish brown-colored stripes and/or greenish brown-colored stippling, streaks and stripes.

Plants of the new *Caladium* differ primarily from plants of the female parent, 'Florida Moonlight', in the following characteristics:

1. Leaves of plants of the new *Caladium* are creamy to greenish white in color variably flushed with pink, variably covered with random pink and/or white-colored spots and proximally, variably mottled with dark green-colored markings whereas leaves of plants of 'Florida Moonlight' are greenish white in color.
2. Leaf petioles of plants of the new *Caladium* are almost black in color with green or tannish brown-colored stripes and/or greenish brown-colored stippling, streaks and stripes whereas leaf petioles of plants of 'Florida Moonlight' are tannish pink in color with greenish brown-colored stippling, stripes and tessellations.

Plants of the new *Caladium* differ primarily from plants of the male parent, 'Splash of Wine', in the following characteristics:

1. Plants of the new *Caladium* are larger than plants of 'Splash of Wine'.
2. Leaves of plants of the new *Caladium* are creamy to greenish white in color variably flushed with pink, variably covered with random pink and/or white-colored spots and proximally, variably mottled with dark green-colored markings whereas leaves of plants of 'Splash of Wine' have dark green-colored venation with interveinal areas that are greenish white or white flushed with red and light red in color and densely covered with red purple-colored spots.
3. Leaf petioles of plants of the new *Caladium* are almost black in color with green or tannish brown-colored stripes and/or greenish brown-colored stippling, streaks and stripes whereas leaf petioles of plants of 'Splash of Wine' are tannish pink in color with greenish brown-colored stripes and streaks.

Plants of the new *Caladium* can be compared to plants of *Caladium* X *hortulanum* 'Summer Breeze', disclosed in U.S. Plant Pat. No. 25,420. In side-by-side comparisons, plants of the new *Caladium* differ primarily from plants of 'Summer Breeze' in the following characteristics:

1. Leaves of plants of the new *Caladium* are creamy to greenish white in color variably flushed with pink, variably covered with random pink and/or white-colored spots and proximally, variably mottled with dark green-colored markings whereas leaves of plants of 'Summer Breeze' are white to creamy white in color with a central pink-colored blush, pink-colored venation and green-colored margins.
2. Leaf petioles of plants of the new *Caladium* are almost black in color with green or tannish brown-colored stripes and/or greenish brown-colored stippling, streaks and stripes whereas leaf petioles of plants of 'Summer Breeze' are pink to tannish pink in color with faint greenish brown-colored streaks, stippling and tessellations.

Plants of the new *Caladium* can also be compared to plants of *Caladium* X *hortulanum* 'Raspberry Moon', disclosed in U.S. Plant Pat. No. 20,069. In side-by-side comparisons, plants of the new *Caladium* differ primarily from plants of 'Raspberry Moon' in the following characteristics:

1. Leaves of plants of the new *Caladium* are creamy to greenish white in color variably flushed with pink, variably covered with random pink and/or white-colored spots and proximally, variably mottled with dark green-colored markings whereas leaves of plants of 'Raspberry Moon' are lime green in color with random dark green and raspberry red-colored coalescing spots and blotches.
2. Leaf petioles of plants of the new *Caladium* are almost black in color with green or tannish brown-colored stripes and/or greenish brown-colored stippling, streaks and stripes whereas leaf petioles of plants of 'Raspberry Moon' are tannish pink in color with darker-colored streaks and tessellations.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'CRM FCY OF15-76' grown in a container that has had its tuber de-eyed prior to planting.

Figure 2:
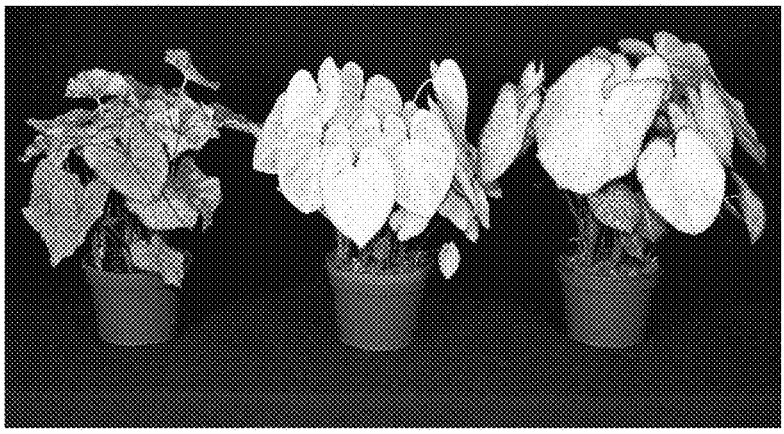

The photograph at the top of the second sheet (FIG. 2) is side perspective view of typical plants of the female parent, 'Florida Moonlight' (right), 'CRM FCY OF15-76' (center) and the male parent, 'Splash of Wine' (left).

Figure 3:
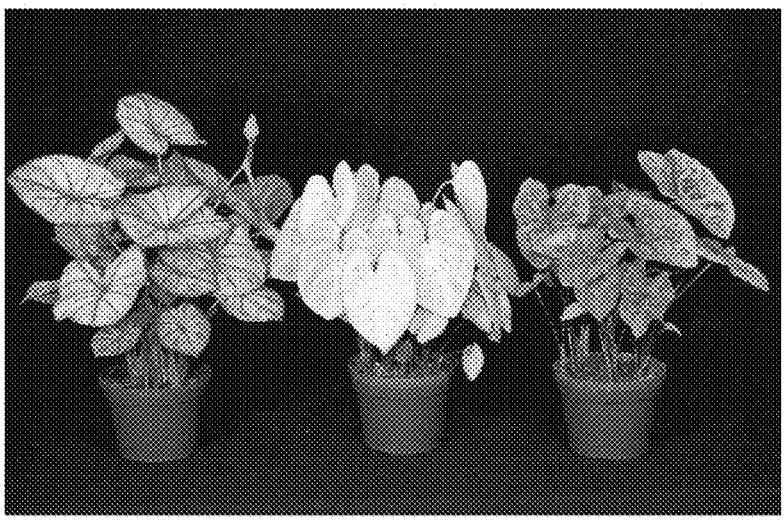

The photograph at the bottom of the second sheet (FIG. 3) is side perspective view of typical plants of 'Summer Breeze' (left), 'CRM FCY OF15-76' (center) and 'Raspberry Moon' (right).

Figure 4:
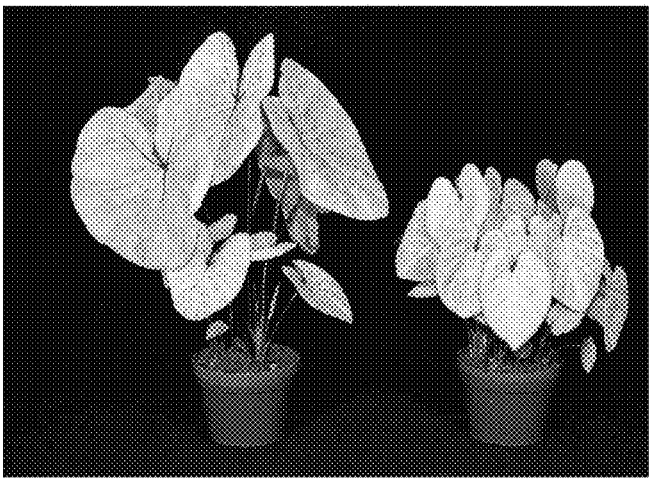

The photograph at the top of the third sheet (FIG. 4) is a comparison view of typical plants of 'CRM FCY OF15-76' grown in containers, the plant on the left has not had its tuber de-eyed and the plant on the right has had its tuber de-eyed prior to planting.

Figure 5:
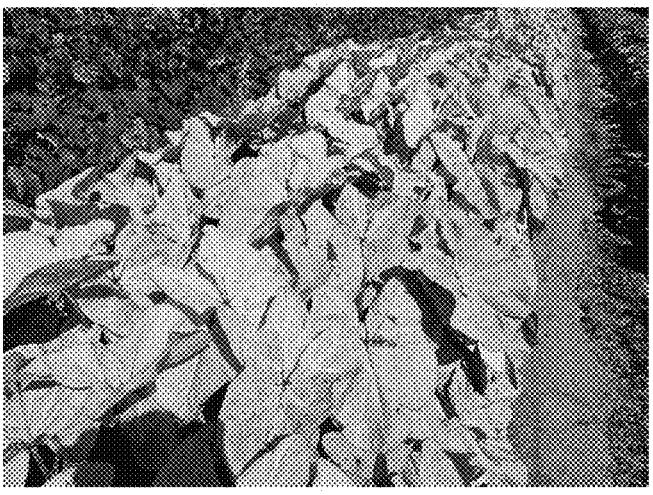

The photograph at the bottom of the third sheet (FIG. 5) is a side perspective view of typical plants of 'CRM FCY OF15-76' grown in an open production field.

Figure 6:
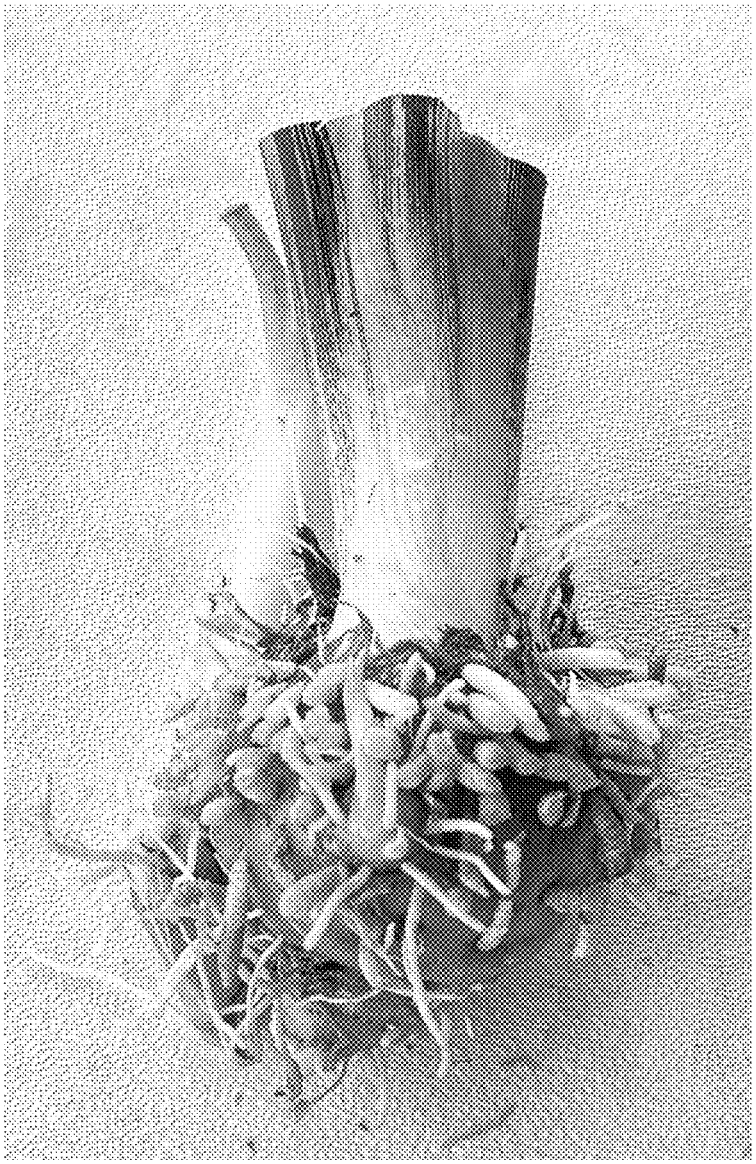

The photograph on the fourth sheet (FIG. 6) is a close-up view of typical freshly-harvested tubers with roots and leaf petioles of 'CRM FCY OF15-76'.

Figure 7:
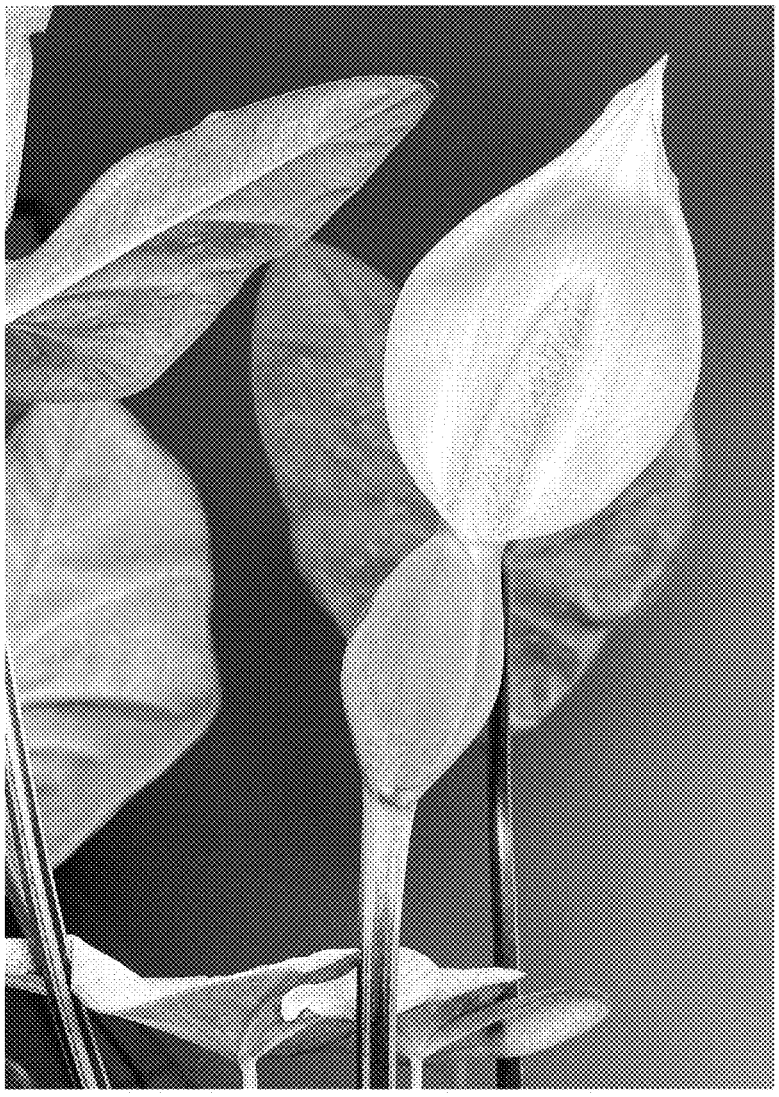

The photograph on the fifth sheet (FIG. 7) is a close-up view of a typical inflorescence of 'CRM FCY OF15-76'.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 1,300 μmol. During the production of the outdoor nursery-grown plants, day temperatures ranged from about 29° C. to 35° C., night temperatures ranged from about 23° C. to 26° C. and full sunlight conditions. Plants grown in the shade house were ten weeks old and plants grown in the outdoor nursery were six months old when the photographs and the detailed description were taken. In the following description, color references are made to The Royal Horticultural Society Colour Chart, 2001 and 2015 Editions, except where general terms of ordinary dictionary significance are used.

Botanical classification: *Caladium* X *hortulanum* 'CRM FCY OF15-76'.

Parentage:

*Female, or seed, parent.*—*Caladium* X *hortulanum* 'Florida Moonlight' disclosed in U.S. Plant Pat. No. 14,565.

*Male, or pollen, parent.*—*Caladium* X *hortulanum* 'Splash of Wine', disclosed in U.S. Plant Pat. No. 31,599.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented; individual segments are ovate to somewhat irregular in shape. Height: About 3.2 cm to 3.8 cm. Diameter: About 4.2 cm to 5.2 cm. Segment height: About 1.5 cm to 2 cm. Segment diameter: About 1.5 cm to 1.7 cm. Axillary bud shape: Roughly triangular. Axillary bud height: About 4 mm to 5 mm. Axillary bud width: About 5.2 mm to 6.5 mm. Texture: Thick, starchy; somewhat brittle. Color: Periderm, freshly-harvested: Close to 199C. Periderm, dried: Close to 200D. Epidermis: Initially, close to N179D becoming closer to 159B with subsequent development. Cortical tissue: Close to 4D. Axillary buds: Close to 38B and 38C with faint and sparse markings, close to 202A. Root description: Thick, fleshy contractile roots with few lateral branches; color, typically paper white in color, actual color of the roots is dependent on substrate composition, water quality, fertilizer type and formulation, substrate temperature and physiological age of roots. Rooting habit: Dense.

Plant description:

*Plant type*.—Herbaceous perennial; suitable as a potted plant in containers 15-cm to 25-cm and suitable as a landscape plant in shaded areas.

*Plant and growth habit*.—Intermediate and upright to mounding plant habit; dense, leafy and bushy appearance; vigorous growth habit and rapid growth rate; potted plants finish in saleable form in about seven weeks after planting tubers; leaf petioles and leaves arise from one or more growing points on tubers; leaf petioles initially upright and leaning outwardly with development.

*Plant height, from soil level to top of foliar plane, shade house-grown potted plants, tubers de-eyed*.—About 35 cm to 41 cm.

*Plant height, from soil level to top of foliar plane, shade house-grown potted plants, tubers not de-eyed*.—About 45 cm to 51 cm.

*Plant height, from soil level to top of floral plane, shade house-grown potted plants, tubers de-eyed*.—About 41.4 cm.

*Plant diameter or spread, shade house-grown potted plants, tubers de-eyed*.—About 40 cm to 47 cm.

*Plant diameter or spread, shade house-grown potted plants, tubers not de-eyed*.—About 44 cm to 55 cm.

*Number of shoots per plant, shade house-grown potted plants, tubers de-eyed*.—About five to eight develop per #1 tuber.

*Number of shoots per plant, shade house-grown potted plants, tubers not de-eyed*.—About two to three develop per #1 tuber.

*Cataphylls, shade house-grown potted plants*.—Length: About 4.9 cm to 5.9 cm. Width: About 1 cm to 1.8 cm. Shape: Narrowly elliptic or wedge-shaped. Apex: Variable, obtuse, acuminate or emarginate. Base: Sheathing the stem. Texture and luster, outer and inner surfaces: Smooth, glabrous; glossy. Color, outer surface: Close to N170D, 199D and 155C tinged with close to 160D, and marbled, streaked and stippled with close to 200A tinged with 147A and/or 202A; color becoming closer to 200C and 200D with subsequent development. Color, inner surface: Close to N155D with colors and color patterns from outer surface visible.

Leaf description:

*Arrangement and type*.—Alternate; simple; fancy-type.

*Length, shade house-grown potted plants, tubers de-eyed*.—About 13 cm to 16 cm.

*Length, shade house-grown potted plants, tubers not de-eyed*.—About 20 cm to 25 cm.

*Width, shade house-grown potted plants, tubers de-eyed*.—About 8.4 cm to 10.4 cm.

*Width, shade house-grown potted plants, tubers not de-eyed*.—About 14 cm to 19 cm.

*Shape*.—Ovate, broadly ovate to cordate.

*Apex*.—Acute, acuminate.

*Base*.—Sagittate-peltate; cordate.

*Margin*.—Entire; mostly flat with broad undulations.

*Texture and luster, upper surface*.—Smooth, glabrous; leathery; dull sheen.

*Texture and luster, lower surface*.—Smooth, glabrous with veins slightly glaucous; leathery; dull sheen.

*Venation pattern*.—Pinnate and palmate.

*Color, shade house-grown potted plants*.—Leaf colors and patterns vary between leaves on the same plant; both upper and lower surfaces are attractive. When developing and fully expanded leaves, upper surface: Background color: Close to 157C, 157D, 151B, 151C, 147B and/or 147C variably flushed with close to 185D; variable and random spots, close to 185D or 155C. Margins: Close to 146A, 146B, 187A, 187B, 187C and/or 187D. Basal notch: Close to 187B and 187C. Leaf petiole junction: Close to N186B tinged with close to 177A with adjacent variable mottling and flecks, close to 147A. Midvein: Close to 145A, 145B and/or 145C variably flushed with close to 177B (mostly proximally), streaked with close to 146A and 146B and surrounded with close to 157C and 157D. Primary lateral venation: Close to 146B, 147A, and/or 145B to 145C variably tinged with close to N186B, 177A and 177B, streaked and flecked with close to 146B and 146C and surrounded with close to 157D. Secondary lateral venation: Close to 147B, 146A, 146B and 146C tinged with close to 147C and surrounded by 157B and 157C. When developing and fully expanded leaves, lower surface: Background color: Close to 157D, 147C and 147D variably tinged with close to 139D, close to N155C or N155D variably tinged with close to 63D, close to 191A and 191B variably tinged with close to 189A (proximally); variable and random spots, close to 63C, 63D or 155C. Margins: Close to 187A, 187B, 187C and/or 187D. Basal notch: Close to 187B. Midvein: Close to 147D tinged with close to 177B and 177C (mostly proximally) surrounded with close to 157D and/or 145D. Primary lateral venation: Close to 145C and 147C to 147D variably tinged with close to 177B and 177C and/or N187A and surrounded with close to 145D and/or 157D. Secondary lateral venation: Close to 147B to 147C, 146B to 146C, or close to 191A.

*Petioles*.—Aspect: Initially upright and straight and leaning outwardly with development; flexible. Length, shade house-grown potted plants: When tubers are de-eyed, about 25 cm to 36 cm. Length, shade house-grown potted plants: When tubers are not de-eyed, about 27 cm to 38 cm. Diameter, distally, shade house-grown potted plants: When tubers are de-eyed, about 3.5 mm to 4 mm. Diameter, proximally, shade house-grown potted plants: When tubers are de-eyed, about 4.5 mm to 6 mm. Diameter, distally, shade house-grown potted plants: When tubers are de-eyed, about 4.5 mm to 5 mm. Diameter, proximally, shade house-grown potted plants: When tubers are not de-eyed, about 5 mm to 11 mm. Texture and luster: Smooth, glabrous; glossy. Color, shade house-grown potted plants: Close to N170D and 147D stippled, streaked and striped with close to 147A flushed with close to N200A or close to 200A tinged with close to 147A and 202A and stippled, streaked and striped with close to 147B, 147C and 197C; just below the leaf junction, close to N170D and 147D variably tinged with close to 181D with stripes and streaks, close to 200A to 200A tinged with close to 147A. Wing length, shade house-grown potted plants: When tubers are de-eyed, about 4 cm to 7 cm. Wing diameter, shade house-grown potted plants: When tubers are de-eyed, about 4.5 mm to 6.5 mm. Wing length, shade house-grown potted plants: When tubers are not de-eyed, about 5.5 cm to 11 cm. Wing diameter, shade house-grown potted plants: When tubers are not de-eyed, about 6.5 mm to 9 mm. Texture and luster, inner and outer surfaces: Smooth, glabrous; glossy. Wing color, shade house-grown potted plants: Outer surface: Close to N170D, 199D and 155C flushed with close to 160D and stippled and streaked with close to 147A flushed with close to 200B. Inner surface: Close to N155D; colors and patterns on the outer surface are visible on the inner surface.

Inflorescence description: Inflorescences observed on nine week-old shade house-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with mint-camphor note.

*Natural flowering season and flower longevity*.—Plants of the new *Caladium* typically flower during the spring and summer in central Florida; flowers develop about nine weeks after growth commences; inflorescences last about three days before fading; inflorescences persistent.

*Spathe*.—Length, overall: About 13.7 cm. Length, distal open portion: About 9.5 cm. Length, proximal closed portion: About 4.2 cm. Width, distal open portion: About 4.7 cm. Depth, distal open portion: About 1.6 cm. Width, at constriction: About 1.25 cm to 1.5 cm. Width, proximal closed portion: About 2.9 cm. Shape, open portion: Elliptic, ovate. Apex: Acuminate. Base: Acute. Margin: Entire; distally, slightly reflexed. Texture and luster, front surface: Smooth, glabrous; slightly glossy to dull sheen. Texture and luster, rear surface: Smooth, glabrous; slightly glaucous (proximally) and dull sheen. Color, front surface: Distal open portion: Close to 155C; with subsequent development, distally becoming closer to 200D. Proximal closed portion: Close to 148C; proximally, faintly flushed with close to N186C; color does not change with subsequent development. Color, rear surface: Distal open portion: Close to 145D and 155C; color does not change with subsequent development. Proximal closed portion: Close to 147B and 147C; color does not change with subsequent development.

*Spadix*.—Length, overall: About 8.3 cm. Length, male flower zone: About 4.3 cm. Length, sterile zone: About 1.6 cm. Length, female flower zone: About 2.4 cm. Diameter, male flower zone: About 1 cm. Diameter, sterile flower zone: About 6 mm. Diameter, female flower zone: About 1 cm. Shape: Columnar, spindle-shaped. Apex: Rounded to acute. Base: Obtuse. Aspect: Upright. Color, mature, male zone: Close to 159C. Color, mature, sterile zone: Close to 155D. Color, mature, female zone: Close to 155D. Male flowers: Quantity per spadix: About 192. Shape: Obovate. Height: About 3.5 mm. Diameter: About 3 mm. Pollen amount: Abundant. Pollen color: Close to 8D. Female flowers: Quantity per spadix: About 224. Shape: Obovate. Height: About 3 mm. Diameter: About 2 mm. Stigma color: Close to 155D. Ovary color: Close to 158C.

*Scapes*.—Length: About 27.7 cm. Diameter: About 6.5 mm. Strength: Sturdy; somewhat flexible. Aspect: Mostly erect, straight. Texture and luster: Smooth, glabrous; slightly glaucous. Color: Close to 160D and 199C streaked, stippled and striped with close to 200C; just below the spathe, close to 147C streaked, stippled and striped with close to 200B and 200C.

*Seeds and fruits*.—To date, seed and fruit development have not been observed on plants of the new *Caladium*.

Pathogen tolerance/resistance: Plants of the new *Caladium* have been observed to have average tolerance to *Pythium* Root Rot and above average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'CRM FCY OF15-76' as illustrated and described.

* * * * *